(12) United States Patent
Jensen et al.

(10) Patent No.: US 8,282,547 B2
(45) Date of Patent: Oct. 9, 2012

(54) SURGICAL HAND ACCESS APPARATUS

(75) Inventors: David Jensen, Westbrook, CT (US); Thomas Wenchell, Durham, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 125 days.

(21) Appl. No.: 12/846,410

(22) Filed: Jul. 29, 2010

(65) Prior Publication Data

US 2010/0312067 A1     Dec. 9, 2010

Related U.S. Application Data

(63) Continuation of application No. 11/095,340, filed on Mar. 31, 2005, now Pat. No. 7,766,824.

(51) Int. Cl.
*A61B 1/32*     (2006.01)

(52) U.S. Cl. ....................................................... 600/208

(58) Field of Classification Search .......... 600/206–208, 600/200–203; 604/201–246, 167.01–167.04
See application file for complete search history.

(56) References Cited

U.S. PATENT DOCUMENTS

| | | |
|---|---|---|
| 2,305,289 A | 12/1942 | Coburg |
| 3,332,417 A | 7/1967 | Blanford et al. |
| 3,427,226 A | 2/1969 | McNeely |
| 3,427,227 A | 2/1969 | Chamberlin |
| 4,069,913 A | 1/1978 | Harrigan |
| 4,516,578 A | 5/1985 | Shuffield |
| 4,984,564 A | 1/1991 | Yuen |
| 5,159,921 A | 11/1992 | Hoover |
| 5,342,385 A | 8/1994 | Norelli et al. |
| 5,366,478 A | 11/1994 | Brinkerhoff et al. |
| 5,368,545 A | 11/1994 | Schaller et al. |
| 5,411,483 A | 5/1995 | Loomas et al. |
| 5,480,410 A | 1/1996 | Cuschieri et al. |
| 5,514,133 A | 5/1996 | Golub et al. |
| 5,520,610 A | 5/1996 | Giglio et al. |
| 5,522,791 A | 6/1996 | Leyva |
| 5,524,644 A | 6/1996 | Crook |
| 5,526,536 A | 6/1996 | Cartmill |
| 5,545,179 A | 8/1996 | Williamson, IV |
| 5,634,911 A | 6/1997 | Hermann et al. |
| 5,636,645 A | 6/1997 | Ou |
| 5,639,937 A | 6/1997 | Hover et al. |
| 5,640,977 A | 6/1997 | Leahy et al. |
| 5,649,550 A | 7/1997 | Crook |
| 5,653,705 A | 8/1997 | de la Torre et al. |
| 5,672,168 A | 9/1997 | de la Torre et al. |
| 5,741,298 A | 4/1998 | MacLeod |
| 5,803,921 A | 9/1998 | Bonadio |

(Continued)

FOREIGN PATENT DOCUMENTS

DE     3737121     11/1989

(Continued)

*Primary Examiner* — Kevin T Truong
*Assistant Examiner* — Christopher Beccia

(57) ABSTRACT

A surgical access apparatus includes a housing member defining a housing axis and a passageway therethrough, a first seal member mounted across the passageway and having at least one expansible segment adapted to facilitate radial movement of the seal passage during manipulation of the object within the first seal member and a second seal member mounted across the passageway distal of the first seal member and being arranged about a second seal axis radially displaced from the first seal axis. The second seal member includes at least one expansible segment dimensioned to facilitate radial movement of the seal passage of the second seal member during manipulation of the object.

14 Claims, 7 Drawing Sheets

U.S. PATENT DOCUMENTS

| | | | |
|---|---|---|---|
| 5,810,721 A | 9/1998 | Mueller et al. | |
| 5,813,409 A | 9/1998 | Leahy et al. | |
| 5,832,925 A | 11/1998 | Rothrum | |
| 5,853,395 A * | 12/1998 | Crook et al. | 604/174 |
| 5,899,208 A * | 5/1999 | Bonadio | 128/897 |
| 5,906,577 A | 5/1999 | Beane et al. | |
| 5,947,922 A | 9/1999 | MacLeod | |
| 5,957,913 A | 9/1999 | de la Torre et al. | |
| 5,964,781 A | 10/1999 | Mollenauer et al. | |
| 5,997,515 A | 12/1999 | de la Torre et al. | |
| 6,024,736 A | 2/2000 | de la Torre et al. | |
| 6,033,426 A * | 3/2000 | Kaji | 606/213 |
| 6,033,428 A | 3/2000 | Sardella | |
| 6,042,573 A | 3/2000 | Lucey | |
| 6,048,309 A | 4/2000 | Flom et al. | |
| 6,077,288 A | 6/2000 | Shimomura et al. | |
| 6,086,570 A * | 7/2000 | Aboul-Hosn et al. | 604/256 |
| 6,099,505 A | 8/2000 | Ryan et al. | |
| 6,110,154 A | 8/2000 | Shimomura et al. | |
| 6,142,935 A | 11/2000 | Flom et al. | |
| 6,142,936 A * | 11/2000 | Beane et al. | 600/207 |
| 6,149,642 A | 11/2000 | Gerhart et al. | |
| 6,159,200 A | 12/2000 | Verdura et al. | |
| 6,162,172 A * | 12/2000 | Cosgrove et al. | 600/208 |
| 6,238,373 B1 | 5/2001 | de la Torre et al. | |
| 6,254,533 B1 * | 7/2001 | Fadem et al. | 600/208 |
| 6,254,534 B1 | 7/2001 | Butler et al. | |
| 6,315,770 B1 | 11/2001 | de la Torre et al. | |
| 6,319,246 B1 | 11/2001 | de la Torre et al. | |
| 6,382,211 B1 | 5/2002 | Crook | |
| 6,440,063 B1 | 8/2002 | Beane et al. | |
| 6,450,983 B1 * | 9/2002 | Rambo | 602/60 |
| 6,578,577 B2 | 6/2003 | Bonadio et al. | |
| 6,610,031 B1 * | 8/2003 | Chin | 604/167.04 |
| 6,814,700 B1 | 11/2004 | Mueller et al. | |
| 6,840,951 B2 | 1/2005 | de la Torre et al. | |
| 6,846,287 B2 * | 1/2005 | Bonadio et al. | 600/208 |
| 6,981,966 B2 * | 1/2006 | Green et al. | 604/167.02 |
| 7,766,824 B2 * | 8/2010 | Jensen et al. | 600/208 |
| 2001/0047188 A1 | 11/2001 | Bonadio et al. | |
| 2002/0019609 A1 | 2/2002 | McFarlane | |
| 2002/0038077 A1 | 3/2002 | de la Torre et al. | |
| 2002/0072762 A1 | 6/2002 | Bonadio et al. | |
| 2004/0015185 A1 | 1/2004 | Ewers et al. | |
| 2004/0092795 A1 | 5/2004 | Bonadio et al. | |
| 2004/127772 A1 | 7/2004 | Ewers et al. | |
| 2004/0249248 A1 | 12/2004 | Bonadio et al. | |
| 2005/0020884 A1 * | 1/2005 | Hart et al. | 600/206 |
| 2005/0165433 A1 | 7/2005 | Haberland et al. | |

FOREIGN PATENT DOCUMENTS

| | | |
|---|---|---|
| EP | 0950376 | 10/1999 |
| FR | 2 710 270 | 9/1993 |
| GB | 2 071 502 | 9/1981 |
| GB | 2 255 019 | 10/1992 |
| JP | 10-108868 | 4/1998 |
| WO | 95/04202 | 2/1995 |
| WO | 95/07056 | 3/1995 |
| WO | 95/22289 | 8/1995 |
| WO | 95/27445 | 10/1995 |
| WO | 95/27468 | 10/1995 |
| WO | 98/35614 | 8/1998 |
| WO | 98/48724 | 11/1998 |
| WO | 99/25268 | 5/1999 |
| WO | 00/32120 | 6/2000 |
| WO | 00/35356 | 6/2000 |
| WO | 00/54675 | 9/2000 |
| WO | 00/54676 | 9/2000 |
| WO | 00/54677 | 9/2000 |
| WO | 01/08563 | 2/2001 |
| WO | 01/08581 | 2/2001 |

* cited by examiner

SURGICAL HAND ACCESS APPARATUS

CROSS-REFERENCE TO RELATED APPLICATIONS

This application is a continuation of U.S. application, Ser. No. 11/095,340, filed Mar. 31, 2005, now U.S. Pat. No. 7,766,824, "SURGICAL HAND ACCESS APPARATUS" issued on Aug. 3, 2010, the entire contents of which are incorporated herein by reference.

BACKGROUND

1. Field of the Disclosure

The present disclosure relates generally to surgical devices for facilitating sealed access across a body wall and into a body cavity and, more particularly, to a surgical access apparatus adaptable to form a seal about either the surgeon's hand and/or surgical instruments during laparoscopic and endoscopic surgical procedures.

2. Description of the Related Art

Minimally invasive surgical procedures including both endoscopic and laparoscopic procedures permit surgery to be performed on organs, tissues and vessels far removed from an opening within the tissue. Laparoscopic and endoscopic procedures generally require that any instrumentation inserted into the body be sealed, i.e. provisions must be made to ensure that gases do not enter or exit the body through the incision as, e.g., in surgical procedures in which the surgical region is insufflated. These procedures typically employ surgical instruments which are introduced into the body through a cannula. The cannula has a seal assembly associated therewith. The seal assembly provides a substantially fluid tight seal about the instrument to preserve the integrity of the established pneumoperitoneum.

Minimally invasive procedures have several advantages over traditional open surgery, including less patient trauma, reduced recovery time, reduced potential for infection, etc. However, despite its recent success and overall acceptance as a preferred surgical technique, minimally invasive surgery, such as laparoscopy, has several disadvantages. In particular, surgery of this type requires a great deal of surgeon skill in order for the surgeon to manipulate the long narrow endoscopic instruments about a remote site under endoscopic visualization. In addition, in laparoscopic surgery involving the intestinal tract, it is often preferable to manipulate large sections of the intestines to perform the desired procedure. These manipulations are not practical with current laparoscopic tools and procedures accessing the abdominal cavity through a trocar or cannula.

To address these concerns, recent efforts have focused on hand-assisted laparoscopic techniques and procedures. These procedures incorporate both laparoscopic and conventional surgical methodologies. The hand assisted technique is performed in conjunction with a hand access seal which is an enlarged device positionable within the incision in, e.g., the insufflated abdominal cavity. The device includes a seal for forming a seal about the surgeon's arm upon insertion while permitting surgical manipulation of the arm within the cavity. However, known hand access seals are quite cumbersome and incorporate elaborate sealing mechanisms. Moreover, these hand access seals are ill-adapted to accommodate radial manipulation of the surgeon's arm within the seal.

SUMMARY

Accordingly, the present disclosure relates to a surgical access apparatus adaptable to permit the sealed insertion of either the surgeon's hand and/or surgical instruments during laparoscopic and endoscopic surgical procedures. In one preferred embodiment, the surgical access apparatus includes an access member having a passageway therethrough and first and second seal members mounted across the passageway. The first seal member includes an inner seal portion and an outer seal portion. The inner seal portion has an aperture for substantial sealed reception of an object inserted therein and is arranged about a first seal axis. The outer seal portion includes at least one expansible rib dimensioned to facilitate movement of the aperture to a displaced position radially displaced from the first seal axis upon insertion of the object therethrough. The second seal member also has an inner portion defining an aperture for substantial sealed reception of the object and is arranged about a second seal axis radially displaced from the first seal axis. Preferably, the apertures of the first and second seal members are in non-overlapping relation and form a substantial seal within the passageway of the access member in the absence of the object inserted within the aperture of the first member. The first seal member is adapted to move to the displaced position upon insertion of the object therethrough whereby the apertures of the first seal member and the second seal member overlap. The outer seal portion of the first seal member may include a plurality of expansible ribs. The expansible ribs may be arranged along respective lines of intersection with the first seal axis of the first seal member.

In another preferred embodiment, the surgical access apparatus includes an access member having a passageway therethrough and a seal member mounted across the passageway. The seal member includes an inner seal portion and an outer seal portion. The inner seal portion has an aperture for substantial sealed reception of an object inserted therein and is arranged about a seal axis. The outer seal portion includes at least one expansible rib dimensioned to facilitate movement of the aperture to a displaced position radially displaced from the seal axis upon insertion of the object therethrough. The at least one expansible rib is generally arranged along a line of intersection with the seal axis of the seal member. The access member may further include a second seal member mounted adjacent the first seal member. The second seal member has an inner portion defining an aperture for substantial sealed reception of the object and is arranged about a second seal axis radially displaced from the first-mentioned seal axis. The first seal member is preferably adapted to move to the displaced position upon insertion of the object therethrough whereby the apertures of the first seal member and the second seal member overlap.

In another preferred embodiment, the surgical hand access apparatus includes a liner base adapted for insertion through an opening within body tissue for at least partial positioning within the body and an access housing mountable to the liner base. The access housing includes a housing member for positioning outside the body and defines a passageway dimensioned for permitting passage of either a surgeon's hand or arm of a surgeon, a first seal member mounted to the housing member and a second seal member mounted within the housing member adjacent the first seal member. The first seal member includes an inner seal portion and an outer seal portion. The inner seal portion has an aperture for substantial sealed reception of either the surgeon's hand or arm. The second seal member also has an inner portion defining an aperture for substantial sealed reception of either the surgeon's hand or arm. The first and second seal members form a substantial seal within the passageway of the housing member in the absence of the hand or arm of the surgeon. However, during insertion of either the surgeon's hand or arm within the aperture of the first seal member, the inner seal portion of the first seal member is adapted to move to position the aperture thereof in at least partial overlapping relation with the aperture of the second seal member to permit passage of the surgeon's hand or arm through the housing member. The outer seal portion of the first seal member includes at least one expansible rib (preferably, a plurality of ribs) dimensioned to facilitate movement of the aperture of the first seal member to a displaced position radially displaced from the first seal axis.

BRIEF DESCRIPTION OF THE DRAWINGS

Preferred embodiments of the present disclosure will be better appreciated by reference to the drawings wherein.

Preferred embodiments of the present disclosure will be better appreciated by reference to the drawings wherein.

DETAILED DESCRIPTION OF THE PREFERRED EMBODIMENTS

The surgical access apparatus of the present disclosure provides a substantial seal between the body cavity of a patient and the outside atmosphere before, during and after insertion of an object through the apparatus. Moreover, the access apparatus of the present disclosure is adapted for positioning within an incision and may retract the tissue defining the incision to permit access to the underlying tissue. The access apparatus is particularly adapted for accommodating the hand and/or arm of a surgeon during a hand assisted laparoscopic procedure and establishing a gas tight seal with the arm when inserted. However, the access apparatus may be adapted to receive other objects, such as surgical instruments. The access apparatus is further adapted to substantially close in the absence of the object to maintain the integrity of the insufflated peritoneal cavity.

Although the specific focus of this disclosure will be on a preferred laparoscopic procedure, it will be noted that laparoscopic surgery is merely representative of a type of operation wherein a procedure can be performed in a body cavity with access through a body wall.

In the following description, as is traditional the term "proximal" refers to the portion of the instrument closest to the operator, while the term "distal" refers to the portion of the instrument remote from the operator.

Figure 1:
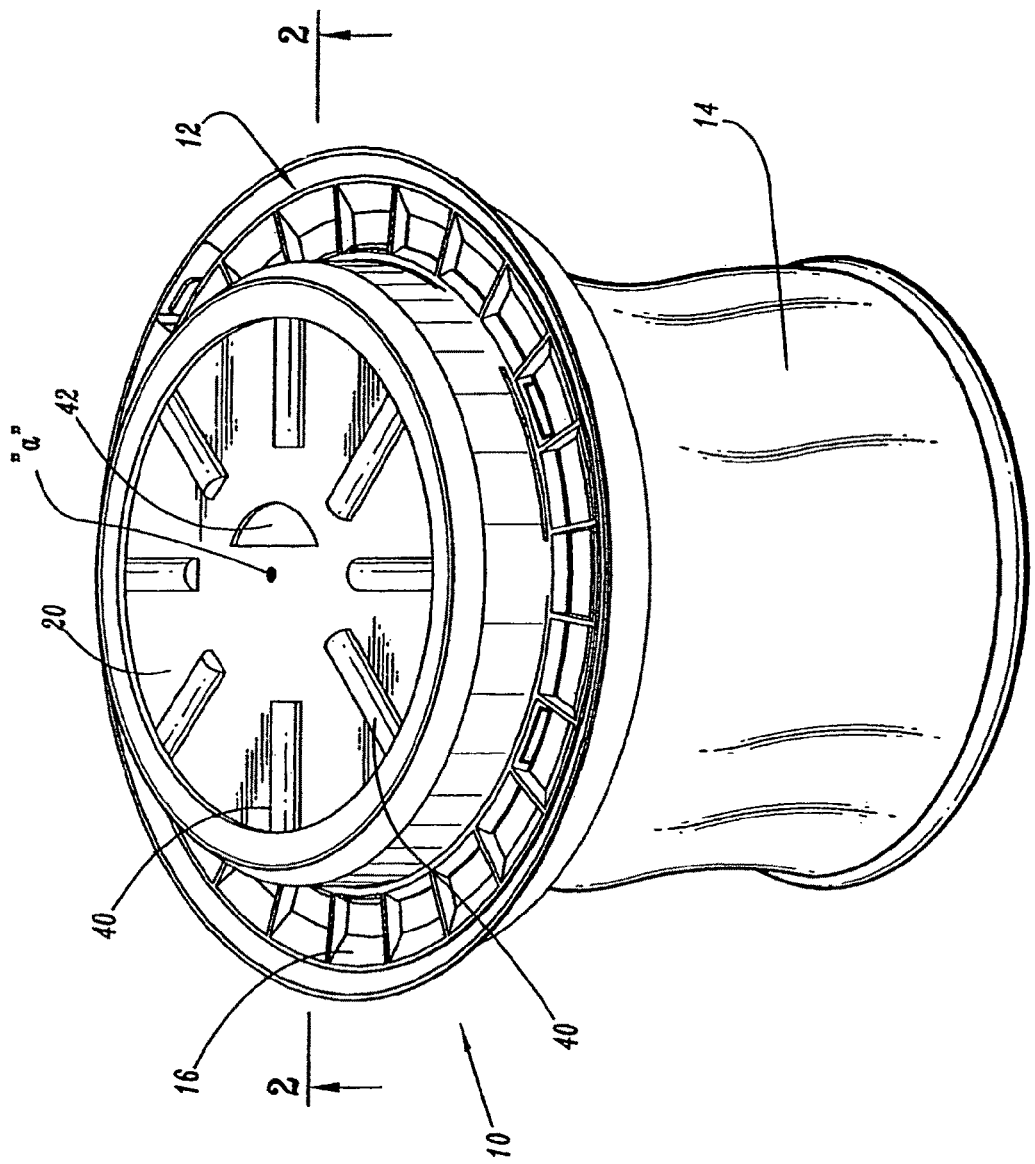
FIG. 1 is a perspective of the hand access apparatus in accordance with the principles of the present disclosure illustrating the access housing and liner base.
Figure 2:
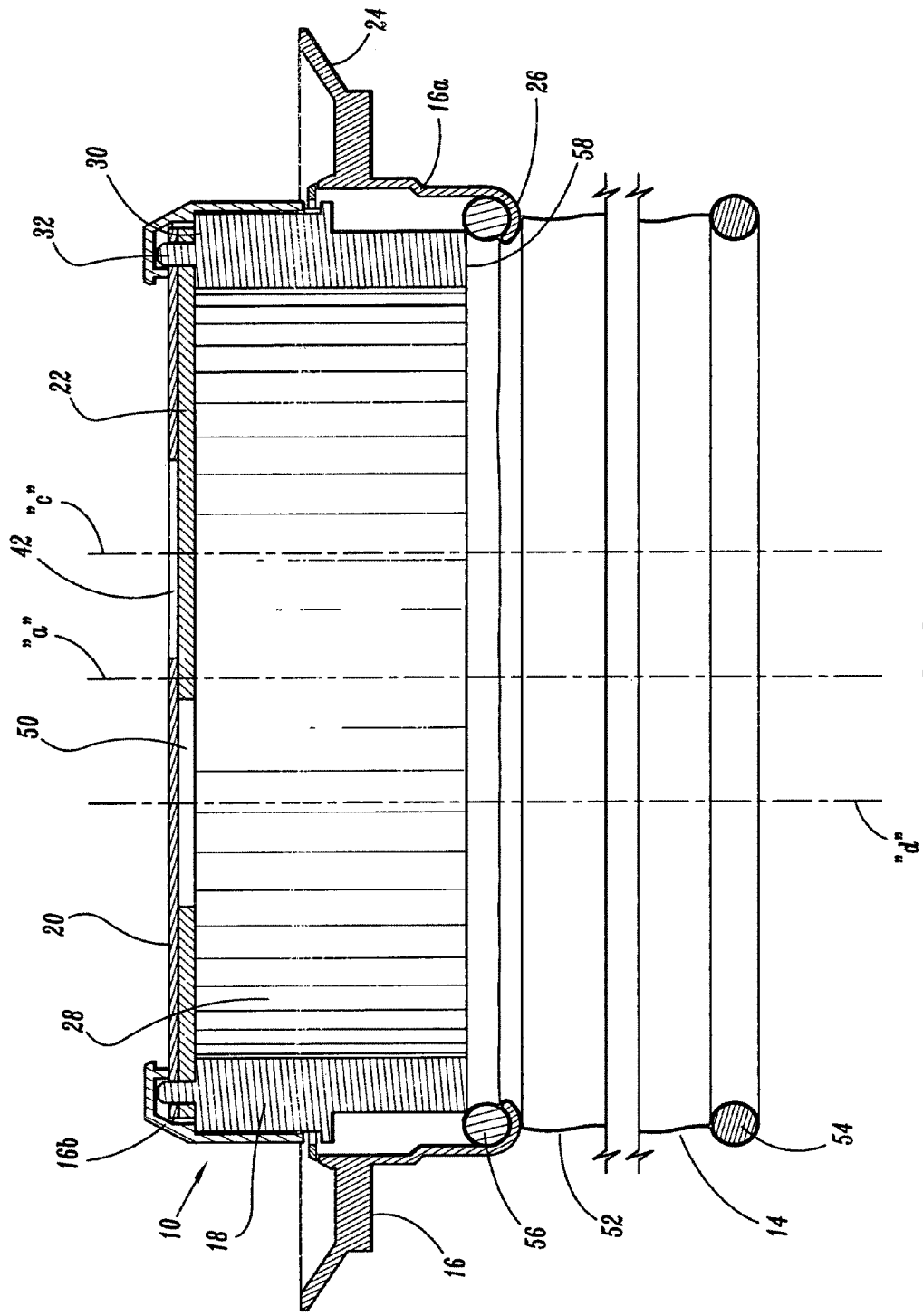
FIG. 2 is a cross sectional view of the access apparatus in accordance with the embodiment of FIG. 1 taken along lines 2-2 of FIG. 1.

Referring now to FIGS. 1-2, hand access apparatus 10 includes two main components, namely, access housing 12 and liner base 14 which is mounted to the access housing 12.

Access housing 12 is positioned external to the body, preferably, in contact with the outer skin of the body and consists of outer frame or housing member 16, seal support 18 disposed within the housing member 16 and first and second seals 20, 22. Housing member 16 preferably defines outer flange 24 dimensioned for engagement by the surgeon and lower U-shaped flange 26. U-shaped flange 26 contacts the skin of the patient upon application of access apparatus 10. U-shaped flange 26 also serves to mount liner base 14. Housing member 16 defines housing axis "a" and internal longitudinal passageway 28 extending through the housing member 16. Housing member 16 may be a single piece component or alternatively incorporate multiple pieces assembled together by conventional means. In one preferred embodiment, housing member 16 incorporates two components 16a, 16b as depicted in FIG. 2. Housing component 16b serves as a cover for enclosing first and second seals 20, 22 and is connected to housing component 16a in fixed relation.

Seal support 18 of access housing 12 is an elongated annular collar which extends at least partially within housing member 16. The upper surface 30 of seal support 18 includes a plurality (two are shown) of upstanding posts 32 peripherally spaced about the periphery of the upper surface 30.

Figure 3:
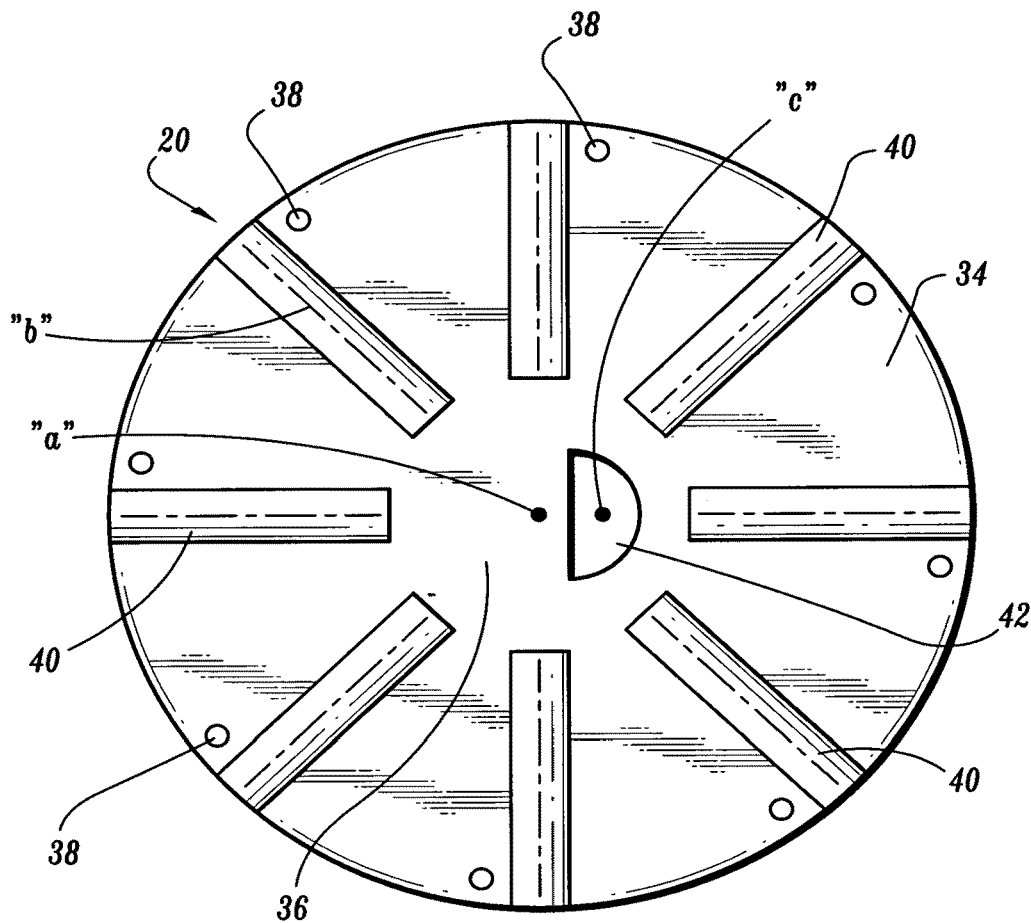
FIG. 3 is a top plan view of a first seal within the access housing.
Figure 4:
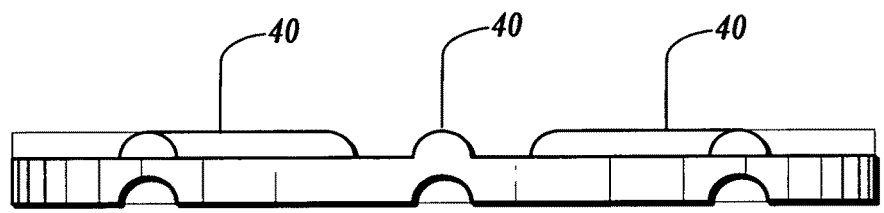
FIG. 4 is a side plan view of the first seal.

Referring now to FIGS. 3-4, in conjunction with FIGS. 1-2, first seal 16 includes outer seal portion 34 and inner seal portion 36. Outer seal portion 34 defines a plurality of apertures 38 which receive corresponding posts 32 of seal support 18 to mount first seal 20 to the seal support 18. Outer seal portion 34 also includes a plurality of ribs 40 radially displaced about the outer seal portion 34. Ribs 40 define an undulating arrangement as shown in FIG. 4. The undulating arrangement permits expansion of outer seal portion 34 particularly during offset manipulation of the object relative to housing axis "a". Ribs 40 are each preferably arranged along a line of intersection "b" with housing axis "a" to permit uniform expansion and movement of first seal 20. Ribs 40 may take other shapes and forms such as, for example, a sinusoidal configuration, pyramidal, convex, concave etc. . .

Inner seal portion 36 defines internal aperture or opening 42. Aperture 42 is arranged about first seal axis "c" (FIG. 2) which is preferably radially offset from housing axis "a". Aperture 42 may be any suitable geometrical shape including circular, elliptical, square, rectangular, or any other polygonal arrangement. In the preferred embodiment, aperture 42 is generally D-shaped. Inner seal portion 36 is adapted to radially move upon insertion of an object though aperture 42 as facilitated by ribs 40 to permit the aperture 42 to assume a position in general alignment with housing axis "a".

Figure 5:
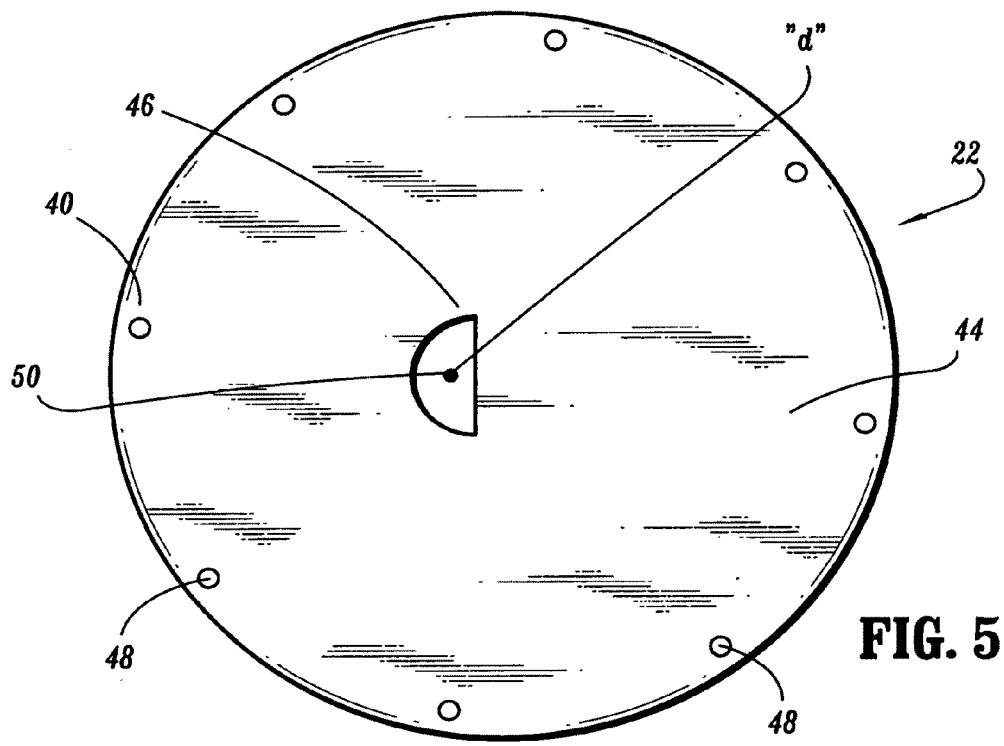
FIG. 5 is a top plan view of a second seal within the access housing.
Figure 5A:
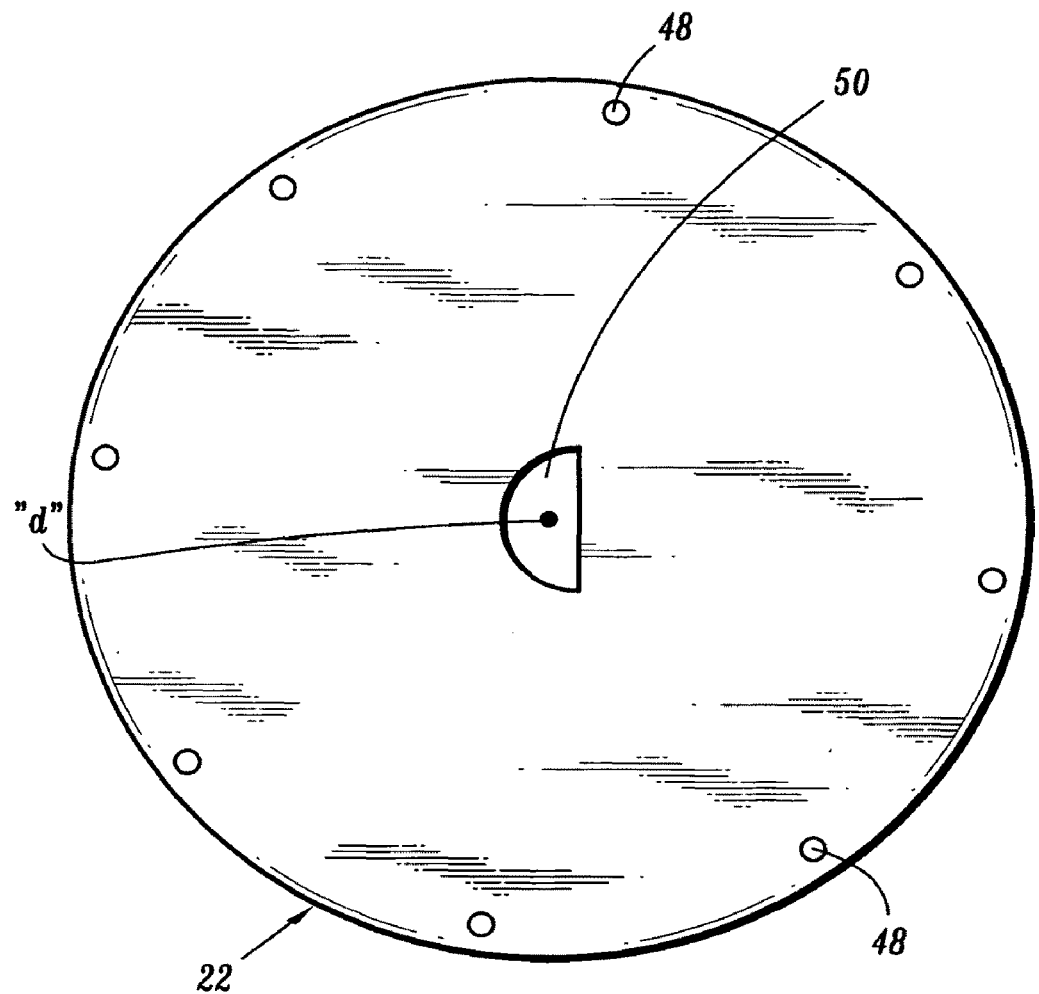
FIG. 5A is a top plan view of an alternate embodiment of the second seal.

With reference to FIG. 5, in conjunction with FIGS. 1-2, second seal 22 includes outer seal portion 44 and inner seal portion 46. Outer seal portion 44 also includes apertures 48 disposed about its periphery for reception of posts 32 of seal support 18 to mount the second seal 22 within housing member 16. Inner seal portion 46 defines opening or aperture 50 which may be of any geometrical shape, but, preferably, is generally D-shaped. Aperture 50 is arranged to be a mirror image of aperture 42 of first seal 20. Aperture 50 is arranged about second seal axis "d" which is radially offset from housing axis "a". Alternatively, as depicted in FIG. 5A, aperture 50 may be centrally located within second seal 22 with second seal axis "d" coincident with axis "a" of housing member 16. This arrangement may minimize the degree of movement required by first seal 20 and also positions the object in the center of housing member 16 during use. Second seal 22 may optionally include expansible ribs of the type aforedescribed in connection with first seal 20.

First and second seals 20, 22 are each adapted to form a substantial seal about an object inserted through their apertures 42, 50 and may stretch to accommodate larger size objects. First and second seals 20, 22 are preferably in juxtaposed contacting relation. First and second seals 20, 22 may be formed of an elastomeric material including commercially available MONOPRENE™. In one preferred embodiment, seals 20, 22 are fabricated from a resilient material, e.g., polyisoprene, with each having at least one layer of fabric material positioned adjacent the resilient material. Seals 20, 22 may be fabricated from an elastomeric material molded with a fabric material. A friction resisting coating may be applied to seals 20, 22. Such seal is disclosed in commonly-assigned U.S. patent application Ser. No. 10/165,373 filed Jun. 6, 2002, the contents of which are incorporated in its entirety by reference.

Figure 6:
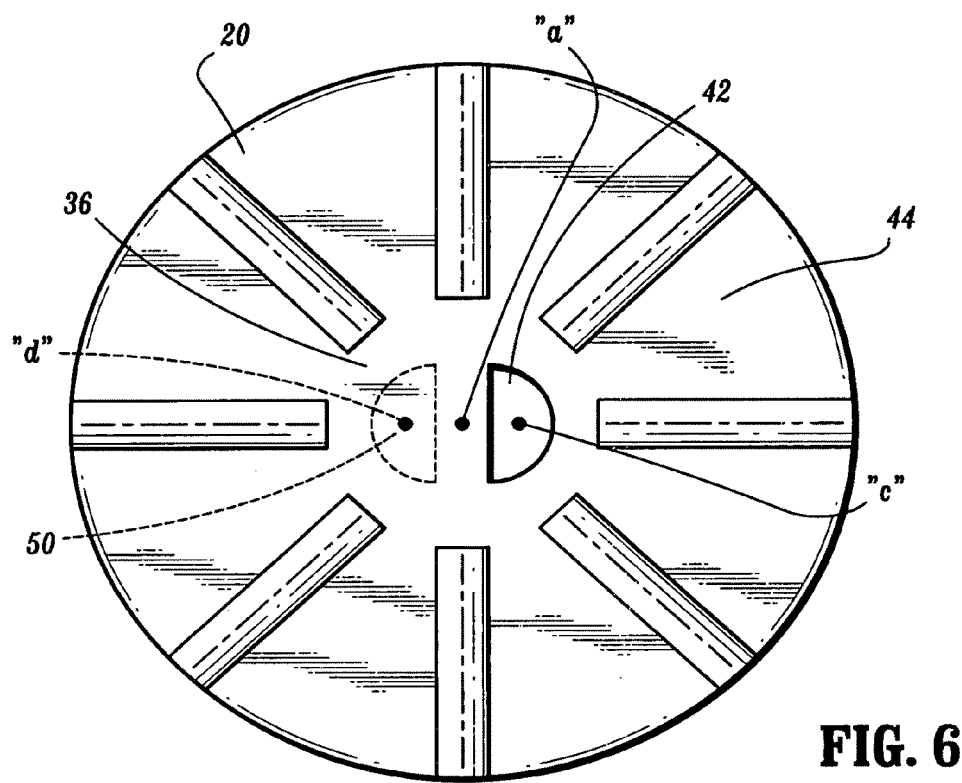
FIG. 6 is a top plan view of the first and second seals with the second seal depicted in phantom.

FIG. 6 illustrates in plan view the arrangement of first and second seals 20, 22 (with second seal 22 shown in phantom) prior to insertion of an object within the apertures 42, 50 of the seals 20, 22. As shown, apertures 42, 50 of first and second seals 20, 22 are in non-overlapping relation, and arranged so that the respective apertures of the first and second seal do not overlap. With this arrangement and with first and second seals 20, 22 in contacting relation, the seals 20, 22 substantially seal longitudinal passageway 28 of housing member 16 to prevent escape of insufflation gases through access housing 12.

Referring again to FIGS. 1-2, liner base 14 of access apparatus 10 will be discussed. Liner base 14 is intended for positioning within the incision of the patient to line the incision and/or retract the tissue defining the incision thereby providing access to the underlying body cavity. Liner base 14 includes liner member 52, and lower ring 54 and upper ring 56 mounted to respective ends of liner member 52. Liner member 52 may be a sheet of flexible material including, for example, polyethylene, polypropylene, etc., arranged in a tubular or sleeve-like configuration.

Liner member 52 may also include an elastomeric material and may incorporate rigid runners embedded within the material to increase its rigidity. Although in the preferred embodiment, liner member 52 is tubular, it is envisioned that the liner member 52 may incorporate several pieces, e.g., individual tabs or the like. Liner member 52 may or may not be impervious to fluids. Liner member 52 is adapted to line the incision so as to prevent contamination of the incision by any tissue which may be removed through the access apparatus, or in the course of the surgery. Generally, liner member 52 may also serve to retract the incision during placement of the liner base 14, so that the patient's skin, fascia, and other tissue are drawn back, allowing access to the surgical site.

Lower ring 54 of liner member 52 is adapted for positioning through the incision and beneath the abdominal wall to engage the interior wall portions to thereby secure liner base 14 relative to the incision. Lower ring 54 is preferably flexible to facilitate passage through the incision and possesses sufficient resiliency to return to its original configuration upon entering the abdominal cavity. Lower ring 54 is preferably annular or ring-like in configuration and may be fabricated from a resilient or elastomeric material. Lower ring 54 may be fixedly secured to the end of liner member 52 through conventional means.

Upper ring 56 is substantially identical to lower ring 54, i.e., upper ring 56 is also annular or ring-like in configuration and is attached to the other end of liner member 52 by conventional means. Upper ring 56 is received within U-shaped flange 26 of access housing 12 and is secured between the flange 26 and lower surface 58 of seal support 18 to secure liner base 14 to access housing 12. Other means for attaching upper ring 56 to access housing 12 are also envisioned.

In further embodiments, seal support 18 discussed above in connection with FIGS. 1-9 is mounted to a different base for retracting the incision and preferably lining the incision. For example, the base 14 may comprise a flexible sleeve for lining the incision and an inflatable member at a proximal end of the sleeve for tensioning the sleeve. Other structures for the base 14 may be used as appreciated by those of ordinary skill in the art. The access apparatus 10 discussed above may also include an additional seal for sealing around the object inserted through the apparatus, such as a septum seal.

Operation

Figure 7:
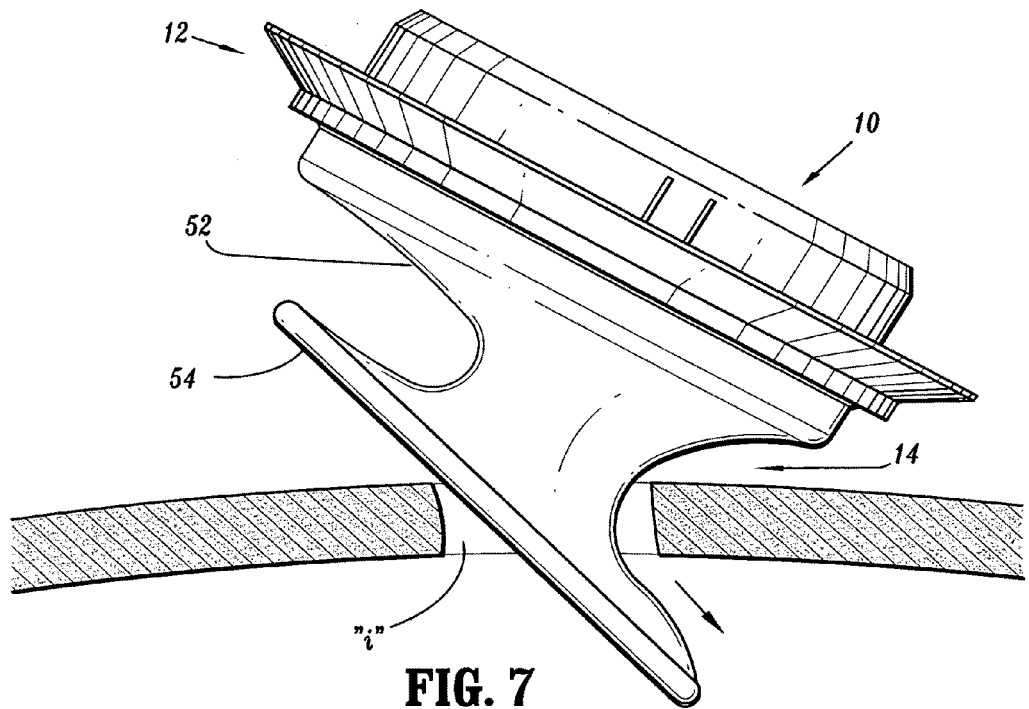
FIGS. 7-8 are views illustrating insertion of the hand access apparatus within an incision.
Figure 8:
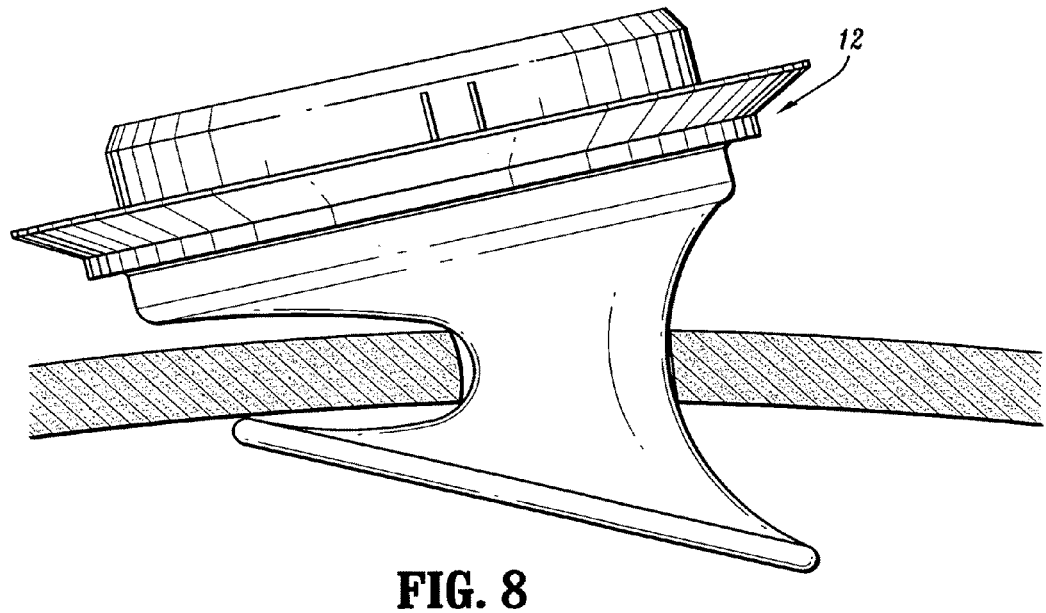

The use of the access apparatus 10 in connection with a hand assisted laparoscopic surgical procedure will be discussed. The peritoneal cavity is insufflated and an incision is made within the cavity, with e.g., a trocar, to provide access to the cavity as is conventional in the art. Thereafter, as depicted in FIGS. 7-8, liner base 14 is introduced within the incision. Specifically, lower ring 54 is passed through the incision "i" and placed within the body cavity. As noted, lower ring 54 may be contracted upon itself to facilitate passage through the incision "i" and then released to permit the lower ring 54 to return to its normal condition (under the influences of its inherent resiliency) within the cavity. Liner member 52 extends from lower ring 54 through the incision to line the incision as previously discussed.

Figure 9:
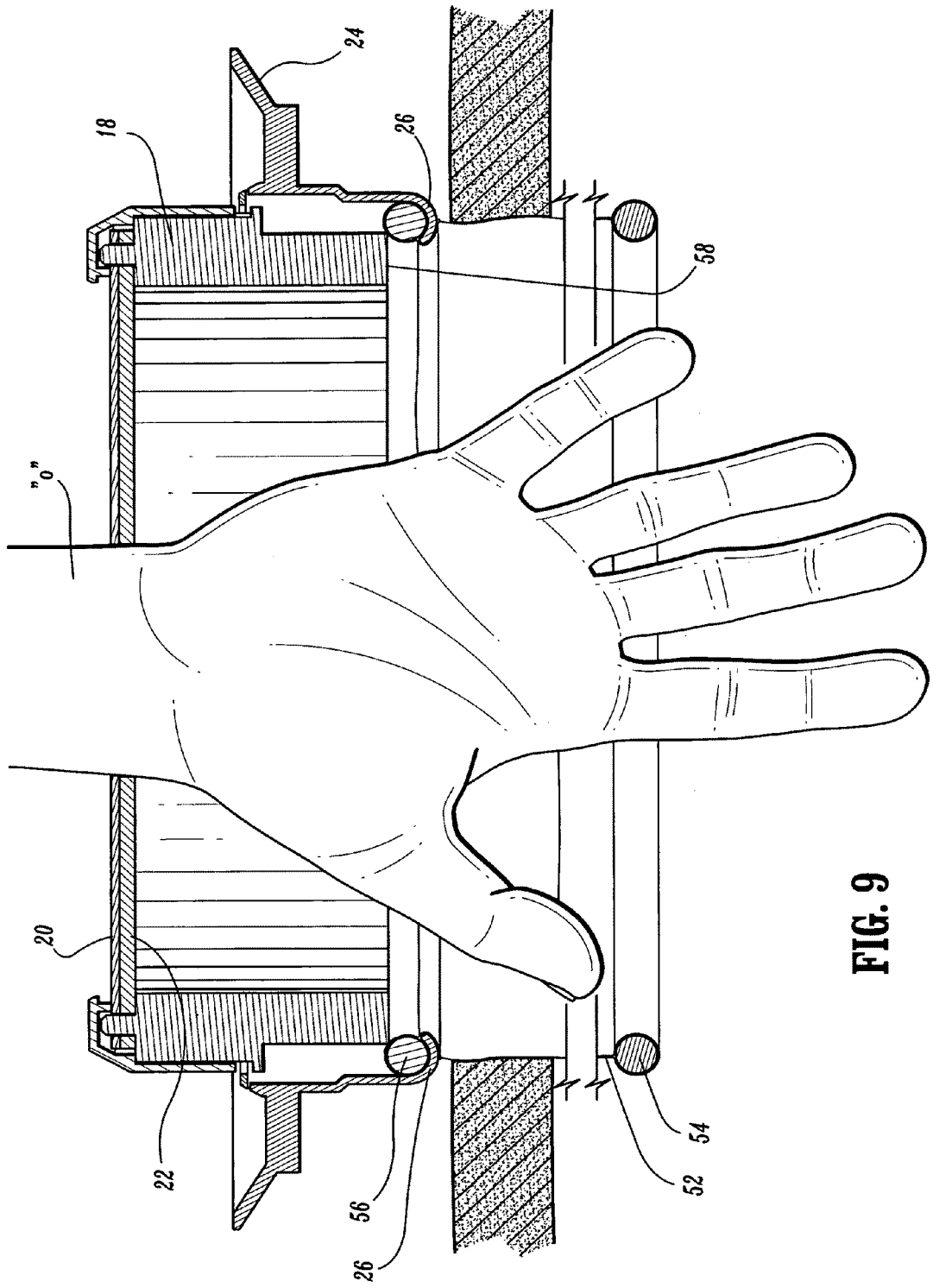
FIG. 9 is a cross-sectional view similar to the view of FIG. 2 illustrating radial movement of the first seal during insertion of an object within the access housing.

With reference to FIG. 9, the procedure is continued by positioning access housing 12 adjacent the external body tissue with the outer surface of U-shaped flange 26 engaging the tissue surrounding the incision. Thereafter, an object such as the surgeon's hand or arm "o" is introduced within access housing 12 and advanced through aperture 42 of first seal 20. As noted, inner seal portion 36 of first seal 20 moves radially as facilitated by expansion of ribs 40 to permit aperture 42 to at least partially overlap with aperture 50 of second seal 22 thereby permitting the surgeon to continue advancing his arm through access housing 12 and liner base 14. The surgeon continues to advance his arm though aperture 50 of second seal 22 and within the abdominal cavity.

With access apparatus 10 in this position of FIG. 9, hand assisted surgery may then be effected by continued advancement of the surgeon's hand and arm through seals 20, 22 of access housing 12 and into the body cavity. Seals 20, 22 form a fluid tight seal about the arm. The desired hand assisted procedure may then be performed.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed:

1. A surgical access apparatus, which comprises:
    a housing member defining a housing axis and a passageway therethrough, the housing dimensioned for passage through tissue;
    a first seal member mounted across the passageway, the first seal member having proximal and distal end faces and a defining a seal passage for permitting passage of a surgical object in substantial sealed reception therewith, the first seal member including at least one expansible segment, the expansible segment including a protruding rib extending in a proximal direction from the proximal end face and a corresponding recess defined within the distal end face and aligned with the protruding rib, the expansible segment arranged to extend radially generally toward and away from the housing axis, and being dimensioned and adapted to facilitate radial movement of the seal passage during manipulation of the object within the first seal member; and a second seal member mounted across the passageway distal of the first seal member, the second seal member defining a seal passage for substantial sealed reception of the object and being arranged about a second seal axis radially displaced from the first seal axis, the second seal member including at least one expansible segment dimensioned to facilitate radial movement of the seal passage of the second seal member during manipulation of the object, the expansible segment of the second seal member including a protruding rib extending in a proximal direction from the proximal end face and a corresponding recess defined within the distal end face and aligned with the protruding rib.

2. The surgical access apparatus according to claim 1 wherein the expansible segment is generally linear.

3. The surgical access apparatus according to claim 2 wherein the expansible segment is generally arranged along a line of intersection with the housing axis.

4. The surgical access apparatus according to claim 1 wherein the first seal member includes a plurality of expansible segments.

5. The surgical access apparatus according to claim 3 wherein the expansible segments are each generally linear.

6. The surgical access apparatus according to claim 5 wherein the expansible segments are each generally arranged along a line of intersection with the housing axis.

7. The surgical access apparatus according to claim 1 wherein the at least one expansible segment of the second seal member is generally arranged along a line of intersection with the housing axis.

8. The surgical access apparatus according to claim 1 wherein the first seal member and the second seal member are arranged so that their respective seal passages do not overlap in the absence of the object positioned therein.

9. The surgical access apparatus according to claim 8 wherein each of the seal passages of the first seal member and the second seal member are generally open passages in the initial condition thereof.

10. The surgical access apparatus according to claim 8 wherein the seal passage of the second seal member is in general alignment with the central housing axis.

11. The surgical access apparatus according to claim 8 wherein the first seal member and the second seal member are dimensioned and adapted to form a substantial seal within the passageway of the housing member in the absence of the object inserted within the aperture of the first seal member.

12. The surgical access apparatus according to claim 1 including a liner base mountable to the housing member, the liner base adapted for insertion through an incision to line the incision and/or retract the tissue defining the incision thereby providing access to the underlying body cavity.

13. The surgical access apparatus according to claim 1 wherein the seal passage of the first seal member is adapted for substantial sealed reception of either a surgeon's hand or arm.

14. The surgical access apparatus according to claim 1 wherein the expansible segments define one of an undulating, sinusoidal, pyramidal, convex, or concave configuration.

* * * * *